United States Patent
Couchou-Meillot

(10) Patent No.: US 12,078,521 B2
(45) Date of Patent: Sep. 3, 2024

(54) DEVICE FOR DETERMINING A VOLUME OF LIQUID IN A FLUID SAMPLE

(71) Applicant: TotalEnergies SE, Courbevoie (FR)

(72) Inventor: Gilles Couchou-Meillot, Pau (FR)

(73) Assignee: TotalEnergies OneTech, Courbevoie (FR)

( * ) Notice: Subject to any disclaimer, the term of this patent is extended or adjusted under 35 U.S.C. 154(b) by 275 days.

(21) Appl. No.: 17/612,823

(22) PCT Filed: May 22, 2019

(86) PCT No.: PCT/IB2019/000749
§ 371 (c)(1),
(2) Date: Nov. 19, 2021

(87) PCT Pub. No.: WO2020/234619
PCT Pub. Date: Nov. 26, 2020

(65) Prior Publication Data
US 2022/0221319 A1    Jul. 14, 2022

(51) Int. Cl.
*G01L 19/00*    (2006.01)
*G01F 19/00*    (2006.01)

(52) U.S. Cl.
CPC .................................. *G01F 19/00* (2013.01)

(58) Field of Classification Search
CPC ...................................................... G01F 19/00
See application file for complete search history.

(56) References Cited

U.S. PATENT DOCUMENTS

| 5,540,087 A * | 7/1996 | Bickert .............. G01N 33/2823 73/53.05 |
| 9,291,585 B2 | 3/2016 | Singh et al. |
| 2008/0016944 A1* | 1/2008 | Legrand ............. G01N 33/2823 73/25.01 |

(Continued)

FOREIGN PATENT DOCUMENTS

| EP | 1677100 B1 | 3/2010 | |
| FR | 2721838 A1 * | 1/1996 | ............... B04C 5/04 |

(Continued)

OTHER PUBLICATIONS

Kedziora-Koch, K., et al., "Needle-based extraction techniques with protected sorbent as powerful sample preparation tools to gas chromatographie analysis: Trends in application," Journal of Chromatography A, Elsevier, Amsterdam, NL, vol. 1565, Jun. 19, 2018.

(Continued)

*Primary Examiner* — Jamel E Williams
(74) *Attorney, Agent, or Firm* — Hamilton, Brook, Smith & Reynolds, P.C.

(57) ABSTRACT

The invention relates to a device for determining a volume of liquid in a hydrocarbon fluid sample, the device including: a cell (1) comprising an upper part (3) defined by a tubular sidewall (5) and a lower part (4) defined by a closed extremity, the lower part having a conical shape and forming a chamber (12) configured to receive the liquid; and a piston (2) comprising an upper part (15) and a lower part (16), the piston being slidable in the cell and sealing the cell in a gas-tight manner. The invention also relates to a method for determining a volume of liquid in a hydrocarbon fluid sample.

19 Claims, 4 Drawing Sheets

(56) References Cited

U.S. PATENT DOCUMENTS

2013/0233054 A1    9/2013  Oliphant et al.
2017/0227479 A1*   8/2017  Molla ................... G01N 25/02

FOREIGN PATENT DOCUMENTS

| | | | | |
|---|---|---|---|---|
| FR | 2856797 | A1 * | 12/2004 | ......... G01N 33/2823 |
| FR | 2906482 | A1 | 4/2008 | |
| FR | 2909770 | A1 | 6/2008 | |
| KR | 20080044929 | A | 5/2008 | |
| RU | 111294 | U1 | 12/2011 | |
| RU | 2503012 | C2 * | 12/2013 | ............ G01N 11/04 |
| SU | 611137 | A1 | 6/1978 | |
| WO | 2012025840 | A2 | 3/2012 | |
| WO | 2016028378 | A1 | 2/2016 | |
| WO | 2018111945 | A1 | 6/2018 | |
| WO | 2019048899 | A1 | 3/2019 | |

OTHER PUBLICATIONS

Landais, P., et al., "Pyrolysis of Organic Matier in Cold-Seal Pressure Autoclaves. Experimental Approach and Applications," Journal of Analytical and Applied Pyrolysis, 16 (1989) 103-115, Elsevier Science Publishers B.V., Amsterdam.

Michels, R. et al., "Understanding of reservoir gas compositions in a natural case using stepwise semi-open artificial maturation," Marine and Petroleum Geology 19 (2002) 589-599.

International Search Report and Written Opinion of the International Searching Authority for PCT Application No. PCT/IB2019/000804, entitled "A Device for Determining a Volume of Gas in a Sample," mailed Jun. 25, 2020.

Notification of Transmittal of the International Search Report and Written Opinion of the International Searching Authority for PCT Application No. PCT/IB2019/000749, entitled "Device for Determining a Volume of Liquid in a Fluid Sample," mailed Feb. 17, 2020.

* cited by examiner

DEVICE FOR DETERMINING A VOLUME OF LIQUID IN A FLUID SAMPLE

This application is the U.S. National Stage of International Application No. PCT/IB2019/000749, filed May 22, 2019, which designates the U.S., published in English. The entire teachings of the above application are incorporated herein by reference.

TECHNICAL FIELD

The present invention relates to a device for determining a volume of liquid in a fluid sample. The present invention also relates to a method for determining a volume of liquid in a fluid sample, the method being implemented in the above-mentioned device.

TECHNICAL BACKGROUND

Hydrocarbon fluids contained in or recovered from subterranean formations are complex fluids containing many different chemical compounds.

In order to optimize hydrocarbon recovery in a process of extracting hydrocarbons from a subterranean formation, it is necessary to know the physical properties of the hydrocarbon fluid, in order to anticipate its volumetric and phase behavior as it travels from the subterranean formation up to surface capabilities, including separators and pipelines for instance, as well as the volumetric and phase behavior of the portion of the fluid remaining in the subterranean formation.

It is also essential to be able to determine the quantity (volume) of recoverable oil and gas comprised in the (recovered) hydrocarbon fluid.

Therefore, it is important to determine the conditions that allow the separation of gas and oil comprised in the hydrocarbon fluid. For example, the presence of a liquid phase (oil) in a hydrocarbon fluid depends on temperature and pressure conditions in the reservoir which allow the condensation of vapor into liquid.

The behavior of hydrocarbon fluids can be studied by pressure-volume-temperature (PVT) analysis. The PVT analysis is usually performed as follows:
- a chamber having an adjustable volume, for instance owing to a piston, is provided;
- a sample of hydrocarbon fluid is introduced into the chamber under relatively high pressure, and the chamber is sealed;
- the volume of the chamber is increased, e.g. by moving the piston; and
- the pressure and the volume in the chamber are measured.

From this measurement, various properties of the hydrocarbon fluid may be determined.

This conventional method raises a number of practical issues. In particular, due to the high pressure which is applied, it is necessary to use a large piston. This, in turn, implies that the chamber must have a large volume. Therefore, due to the large volume of the chamber, the equipment has a large dead volume, which may result in poor accuracy. In fact, the accuracy decreases as the volume of liquid to be detected decreases, which makes it difficult to measure low volumes of liquid.

Furthermore, to ensure air-tightness between the chamber and means used to visualize and monitor the content of the chamber, the presence of sealants is often necessary. However, these sealants also tend to create dead volumes that negatively affect the accuracy of the measurement.

Documents FR 2 856 797 and FR 2 909 770 describe a device for measuring thermodynamic characteristics of a fluid sample comprising a high-pressure cell equipped with a motorized piston. The cell comprises a specific head wherein a chamber of elongated shape along the axis of the cell is intended to collect the liquid, and means for visualizing the position of the liquid/gas interface.

Document WO 2012/025840 relates to an apparatus for measuring thermodynamic properties of reservoir fluids comprising a modular sensor assembly designed to evaluate a sample of hydrocarbon-containing fluid within a cell body. The modular sensor assembly comprises a cell body having a sample chamber and a density-viscosity sensor located in-situ to measure the density and viscosity of the sample in the sample chamber as a function of pressure and temperature.

Document WO 2016/028378 describes a microfluidic apparatus comprising a microchannel that includes one or more than one vertically oriented segments with a top section having a relatively wide opening and a bottom section having a relatively narrow opening. Each segment further comprises a middle section which tapers down from at least one dimension from the top section to the bottom section. Each segment acts as a PVT cell.

There is thus a need for a device for measuring a volume of liquid in a hydrocarbon fluid sample, which makes it possible to efficiently measure the volume of the liquid with high accuracy, even for very small volumes of liquid.

SUMMARY OF THE INVENTION

It is a first object of the invention to provide a device for determining a volume of liquid in a hydrocarbon fluid sample, the device including:
- a cell comprising an upper part defined by a tubular sidewall and a lower part defined by a closed extremity, the lower part having a conical shape and forming a chamber configured to receive the liquid; and
- a piston comprising an upper part and a lower part, the piston being slidable in the cell and sealing the cell in a gas-tight manner.

According to some embodiments, the closed extremity of the cell has an aperture from 30 to 120°, and preferably from 45 to 75°.

According to some embodiments, the lower part of the cell comprises at least one marking on the peripheral surface of the cone-shaped closed extremity.

According to some embodiments, each marking is the form of a circular arc.

According to some embodiments, the markings are arranged in one or several conical sectors on the peripheral surface of the cone-shaped closed extremity.

According to some embodiments, the markings are arranged in two conical sectors on the peripheral surface of the cone-shaped closed extremity.

According to some embodiments, the lower part of the cell comprises from 2 to 20 markings, and preferably from 5 to 10 markings.

According to some embodiments, the lower part of the piston has a truncated-cone shape in order to be partly slidable within the lower part of the cell.

According to some embodiments, the piston comprises a window oriented towards the cone-shaped closed extremity of the cell.

According to some embodiments, the lower part of the piston has an upper end and a lower end and the lower end has a diameter from 5 to 30 mm.

According to some embodiments, the piston comprises an endoscope configured to connect the window with a monitoring system.

According to some embodiments, a system for illuminating the cell, preferably an optic fiber, is arranged in the piston.

According to some embodiments, the upper part of the cell comprises at least one fluid inlet and at least one fluid outlet.

According to some embodiments, the device comprises at least one pressure sensor in the cell.

According to some embodiments, the upper part of the cell has a length from 10 to 50 cm.

According to some embodiments, the upper part of the cell has an inner diameter from 20 to 50 mm, and preferably from 30 to 40 mm.

According to some embodiments, the lower part of the cell has a height from 10 to 40 mm, and preferably from 20 to 35 mm.

According to some embodiments, the upper part of the piston has a length from 10 to 60 cm According to some embodiments, the upper part of the piston has an outer diameter equal to or less than 50 mm.

According to some embodiments, the lower part of the piston has a height from 2.5 to 37.5 mm, and preferably from 5 to 35 mm.

Another object of the invention is to provide an assembly comprising:
- the device mentioned above; and
- a monitoring system for visually monitoring the content of the chamber, which preferably comprises a camera.

According to some embodiments, the assembly comprises a temperature-regulated enclosure surrounding the cell, the monitoring system being preferably arranged out of the enclosure.

According to some embodiments, the assembly mentioned above, or the device mentioned above, comprise at least one temperature sensor.

Another object of the invention is to provide a method for determining the volume of a liquid in a hydrocarbon fluid sample, the method comprising the steps of:
- introducing a hydrocarbon fluid sample into the cell of the device mentioned above, or to the assembly mentioned above;
- decreasing the pressure inside the cell by sliding the piston in the cell;
- measuring the volume of liquid present in the chamber.

According to some embodiments, the hydrocarbon fluid is a gas condensate.

According to some embodiments, the pressure is decreased by one on or more decrements, each decrement being from 0.1 to 50 bar, preferably from 0.5 to 20 bar, and preferably from 1 to 10 bar, relative to the initial pressure inside the cell (1).

According to some embodiments, the step of measuring the volume of liquid is carried out by visually monitoring the chamber and determining the position of a liquid-gas interface on the peripheral surface of the cone-shaped closed extremity.

According to some embodiments, visually monitoring the chamber is carried out through a window of the piston.

According to some embodiments, the position of the liquid-gas interface is determined owing to at least one marking present on the peripheral surface of the cone-shaped closed extremity.

According to some embodiments, the step of decreasing the pressure and the step of measuring the volume of liquid are repeated a plurality of times.

According to some embodiments, the method is carried out at a constant temperature.

According to some embodiments, the temperature in the cell is from 15 to 200° C., and preferably from 80 to 180° C.

According to some embodiments, the initial pressure in the cell is from 10 to 2 000 bar, and preferably from 10 to 1 500 bar.

According to some embodiments, a volume of liquid equal to or lower than 1 000 μL, preferably equal to or lower than 500 μL, preferably equal to or lower than 100 μL, preferably equal to or lower than 50 μL, preferably equal to or lower than 10 μL, preferably equal to or lower than 1 μL, preferably equal to or lower than 0.5 μL, and preferably equal to or lower than 0.2 μL is measured.

The present invention makes it possible to address the need expressed above. In particular, the invention provides a device for measuring a volume of liquid in a hydrocarbon fluid sample, which makes it possible to efficiently measure the volume of the liquid with high accuracy, even for very small volumes of liquid.

This is achieved by using a device including a cell comprising an upper part and a lower part, the lower part being defined by a closed extremity which is in the shape of a cone and forms a chamber configured to receive a liquid. Due to the shape of this closed extremity, the accurate measurement of small volumes of liquid becomes possible.

In fact, the liquid is accumulated in the chamber formed by the closed extremity.

Advantageously, the presence of markings on the chamber facilitates the measurement of the volume of liquid.

Advantageously, the measurement is made possible due to the presence of a window in the lower part of the piston and due to its connection with a monitoring system.

Furthermore, as the window and the monitoring system are not located in the chamber comprising the liquid, there are no dead volumes that could affect the efficiency and accuracy of the measurement.

DESCRIPTION OF EMBODIMENTS

The invention will now be described in more detail without limitation in the following description.

Device for Determining the Volume of Liquid

The device according to the invention is used to determine the volume of a liquid comprised in a hydrocarbon fluid.

Figure 1:
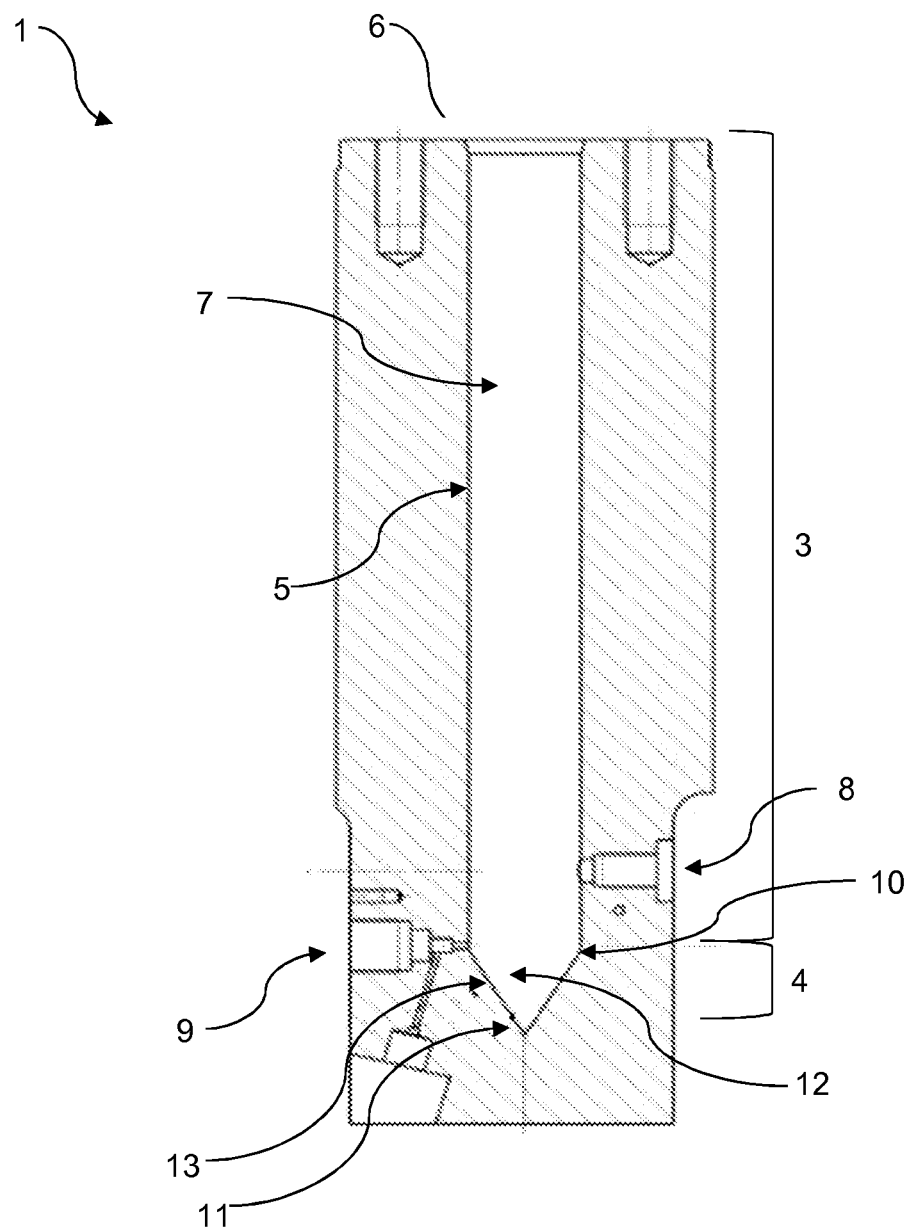
FIG. 1 illustrates a cross-sectional view of the cell of the device according to one embodiment of the invention.
Figure 2:
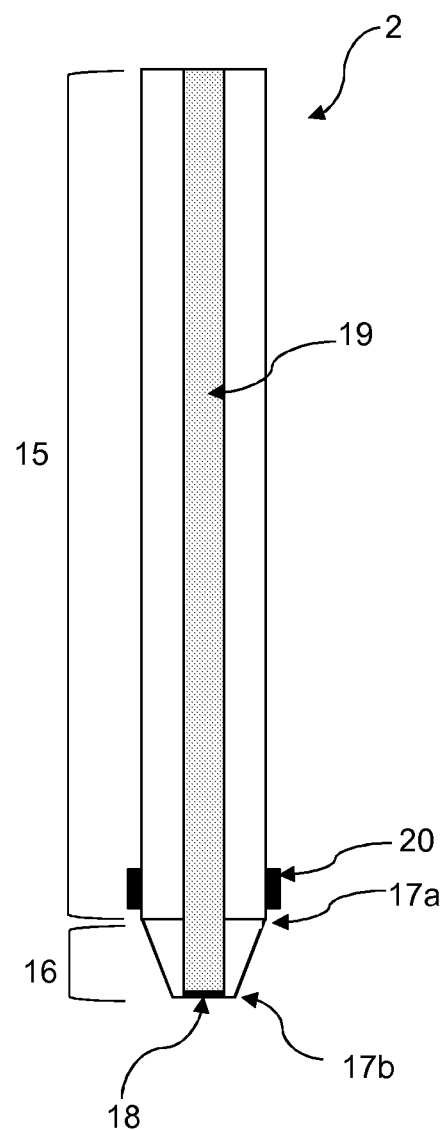
FIG. 2 illustrates a cross-sectional view of the piston of the device according to one embodiment of the invention.

Making reference to FIGS. 1 and 2, the device according to the invention comprises a cell 1 and a piston 2, having a common longitudinal axis. During use, the device according to the invention is placed vertically (the longitudinal axis of the cell 1 being oriented in the vertical direction), as shown in FIG. 1.

The cell 1 comprises an upper part 3 and a lower part 4. The upper part 3 is defined by a tubular sidewall 5 which extends along the longitudinal axis of the cell 1, between an open extremity 6 and the lower part 4 of the cell 1. The tubular sidewall 5 defines an internal space 7, wherein the hydrocarbon fluid sample can be placed.

By the term "tubular" is meant a shape of a cylinder with a circular or non-circular base. For example, the base may be a disc, an oval, a square, a rectangle, a regular or non-regular polygon, or a combination of planar surfaces and/or curved surfaces. Preferably, the base is a circular disc.

The upper part 3 of the cell 1 (or in other words the tubular side wall 5) may have a length from 10 to 50 cm, and preferably from 20 to 40 cm. For example, the upper part 3 of the cell 1 may have a length from 10 to 15 cm; or from 15 to 20 cm; or from 20 to 25 cm; or from 25 to 30 cm; or from 30 to 35 cm; or from 35 to 40 cm; or from 40 to 45 cm; or from 45 to 50 cm.

Furthermore, the upper part 3 of the cell 1 (or in other words the tubular side wall 5) may have an inner diameter from 20 to 50 mm, and preferably from 30 to 40 mm. This inner diameter may notably be from 20 to 22 mm; or from 22 to 24 mm; or from 24 to 26 mm; or from 26 to 28 mm; or from 28 to 30 mm; or from 30 to 32 mm; or from 32 to 34 mm; or from 34 to 36 mm; or from 36 to 38 mm; or from 38 to 40 mm; or from 40 to 42 mm; or from 42 to 44 mm; or from 44 to 46 mm; or from 46 to 48 mm; or from 48 to 50 mm. The inner diameter of the upper part 3 of the cell 1 is the maximum inner dimension of the upper part 3 of the cell 1 in a plane orthogonal to the longitudinal axis.

The upper part 3 of the cell 1 may comprise at least one fluid inlet 8 and at least one fluid outlet 9. Such inlet 8 and outlet 9 may comprise a respective valve. For example, the inlet can be connected to a source of hydrocarbon fluid such as a vessel comprising the hydrocarbon fluid, via a tube or a conduit. Similarly, the outlet can be connected to a different vessel or a cell that makes it possible to evacuate the hydrocarbon fluid sample from the cell 1, this connection preferably being made via a tube or a conduit. Alternatively, the inlet 8 and the outlet 9 may be used to carry out a washing step in order to wash the cell 1 with a fluid that may enter the cell 1 from the inlet 8 and exit the cell 1 from the outlet 9.

The lower part 4 of the cell 1 is defined by a closed extremity which has the shape of a cone. In other words, the lower part 4 is tapered—it comprises a non-tapered end 10 and a tapered or pointed end 11. Thus, the non-tapered end 10 is connected to the upper end 3 of the cell 1 while the tapered end 11 is closed.

The closed extremity forms a chamber 12 which is configured to receive the liquid that is present in the cell 1. Thus, the chamber 12 is in fluid communication with the interior space 7 defined by the tubular sidewall 5.

According to preferred embodiments, the upper part 3 and the lower part 4 of the cell 1 are integrally formed as a single piece.

The lower part 4 of the cell 1 may have a height from 10 to 40 mm, and preferably from 20 to 35 mm. For example, the lower part 4 of the cell 1 may have a height from 10 to 12 mm; or from 12 to 14 mm; or from 14 to 16 mm; or from 16 to 18 mm; or from 18 to 20 mm; or from 20 to 22 mm; or from 22 to 24 mm; or from 24 to 26 mm; or from 26 to 28 mm; or from 28 to 30 mm; 30 to 32 mm; or from 32 to 34 mm; or from 34 to 36 mm; or from 36 to 38 mm; or from 38 to 40 mm. By "height" is meant the perpendicular distance from the top of the cone (tapered end 11) to its base (non-tapered end 10).

As the lower part 4 of the cell 1 is tapered, it has a diameter that decreases from the non-tapered end 10 to the tapered end 11. The diameter of the lower part 4 of the cell 1 at the non-tapered end 10 is preferably the same as the diameter of the upper part 3 of the cell 1. The aperture of the chamber 12 may be from 30 to 120°, and preferably from 45 to 75°. For example, this angle may be from 30 to 35°; or from 35 to 40°; or from 40 to 45°; or from 45 to 50°; or from 50 to 55°; or from 55 to 60°; or from 60 to 65°; or from 65 to 70°; or from 70 to 75°; or from 75 to 80°; or from 80 to 85°; or from 85 to 90°; or from 90 to 120°. The aperture is equal to twice the angle between the peripheral surface 13 of the chamber 12 and the longitudinal axis of the cell 1.

Owing to the aperture recited above, a higher accuracy in the measurement of the volume of liquid based on the height of liquid in the chamber 12 may be achieved, notably when the volume is small.

Figure 3:
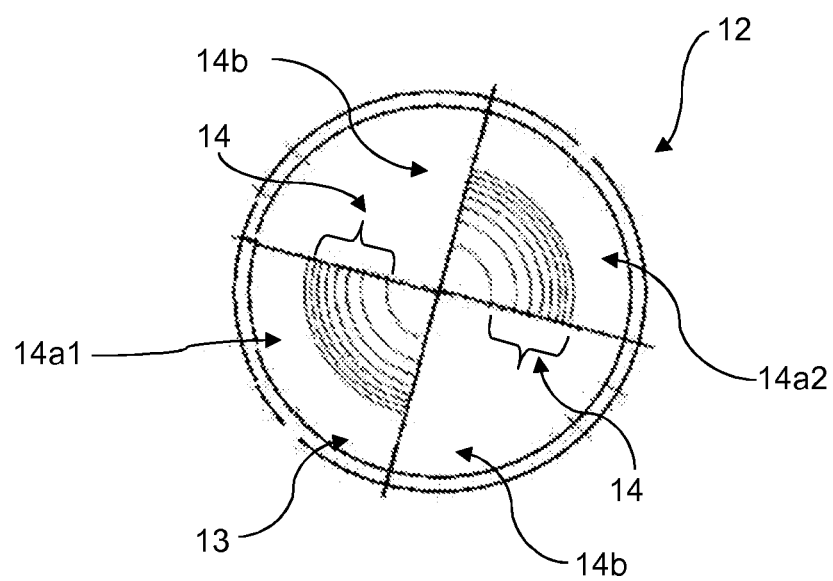
FIG. 3 illustrates a perspective view of the cone-shaped closed extremity of the cell according to one embodiment of the invention.

In order to facilitate the determination of the volume of liquid in the chamber 12, the lower part 4 of the cell 1 may have at least one marking on a peripheral surface 13 of the cone-shaped closed extremity. FIG. 3 illustrates a plurality of markings 14 present on the peripheral surface 13 of the closed extremity. According to some embodiments, the markings are engraved on the peripheral surface 13 of the cone-shaped closed extremity.

Each marking 14 may indicate the diameter of the cone formed by the cone-shaped closed extremity, at the level of the marking 14 in order to determine the height of the liquid inside chamber 12 (or else the interface between the liquid and the gas phase). By "level" is meant a specific point along the longitudinal axis on the peripheral surface 13 of the cone-shaped closed extremity.

The marking 14 may be in the form of at least one circular arc (in other words a segment or a part of a circle) covering at least one part of a peripheral surface 13 of the cone-shaped closed extremity (the shape of the circular arc being illustrated in FIG. 3). The plane containing the circular arc is preferably orthogonal to the longitudinal axis.

It is advantageous if the lower part 4 of the cell 1 presents more than one markings 14 (as illustrated in FIG. 3), notably from 2 to 20 markings 14, and preferably from 5 to 10 markings 14. For example, the lower part 4 of the cell 1 may present from 2 to 4; or from 4 to 6; or from 6 to 8; or from 8 to 10; or from 10 to 12; or from 12 to 14; or from 14 to 16; or from 16 to 18; or from 18 to 20 markings 14.

Therefore, in case more than one markings 14 are present on the lower part 4 of the cell 1, the markings 14 may be located at different levels on the peripheral surface 13 of. By "different levels" is meant different points along the longitudinal axis, on the peripheral surface 13 of the cone-shaped closed extremity.

More particularly, the markings, notably the circular arcs, may be arranged in one or more conical sectors 14a1, 14a2 on the peripheral surface 13 of the cone-shaped closed extremity. According to preferred embodiments, the markings 14 may be arranged in two conical sectors 14a1, 14a2 on the peripheral surface 13 of the cone-shaped closed extremity. Preferably, when the markings 14 are arranged in two conical sectors 14a1, 14a2, these conical sectors are separated from each other by two other conical sectors 14b devoid of markings 14 (as illustrated in FIG. 3).

Furthermore, when the markings 14 are arranged in two (or more) conical sectors 14a1, 14a2, successive markings 14 (along the longitudinal axis) are preferably present in different conical sectors 14a1, 14a2, for example a first marking 14 is present on a first conical sector 14a1, a second marking 14 is present on a second conical sector 14a2, a third marking 14 is present on the first conical sector 14a1 or on a third conical sector (not illustrated in the figures), and so on . . . . In other words, it is preferable that successive markings 14 are not present on the same conical sector 14a1, 14a2, but alternate between the two (or more) conical sectors 14a1, 14a2.

Thus, in some variations, if markings are numbered according to their distance from the lower end of the cone-shaped closed extremity, odd markings are present in a first conical sector 14a1, while even markings are present in a second conical sector 14a2.

This makes it easier to precisely assess the height of liquid by comparing it to the markings.

When the markings are formed as circular arcs, they do not form complete circles on the peripheral surface 13 of the cone-shaped extremity.

According to other embodiments, the markings may be present as complete circles on the peripheral surface 13 of the cone-shaped extremity.

Each marking 14 may be at a distance from 0.1 to 1 cm, and preferably from 0.25 to 0.5 cm from the next marking 14. For example, this distance may be from 0.1 to 0.2 cm; or from 0.2 to 0.3 cm; or from 0.3 to 0.4 cm; or from 0.4 to 0.5 cm; or from 0.5 to 0.6 cm; or from 0.6 to 0.7 cm; or from 0.7 to 0.8 cm; or from 0.8 to 0.9 cm; or from 0.9 to 1 cm.

According to some embodiments, this distance is the same between all successive markings 14.

According to other (preferred) embodiments, this distance (between two successive markings 14) may differ from one couple of successive markings 14 to the next. In this case, each marking 14 may correspond to a specific volume in the cone-shaped closed extremity, the difference between successive markings 14 corresponding to a volume difference. Preferably, this volume difference may be the same between all successive markings 14.

This volume difference between successive markings 14 may be for example from 0.03 to 0.05 µL; or from 0.05 to 1 µL; or from 1 to 5 µL; or from 5 to 10 µL; or from 10 to 25 µL; or from 25 to 50 µL; or from 50 to 75 µL; or from 75 to 100 µL; or from 100 to 150 µL; or from 150 to 200 µL; or from 200 to 250 µL; or from 250 to 300 µL; or from 300 to 350 µL; or from 350 to 400 µL; or from 400 to 450 µL; or from 450 to 500 µL.

For example, the first marking 14 (the marking which is closest to the lower end of the cone-shaped closed extremity) may correspond to a volume of liquid from 0.03 to 5 µL, and preferably from 0.03 to 1 µL.

Furthermore, the last marking 14 (the marking which is farthest from the cone-shaped closed extremity) may correspond to a volume of liquid from 1 500 to 3 000 µL, and preferably from 1 500 to 2 000 µL.

Therefore, when the height of liquid corresponds to a specific marking 14, this may make it possible to directly determine the volume of liquid in the chamber 12, without any further processing.

Alternatively, when the height of liquid is located between two successive markings 14, further processing, for example by using a processing system able to perform a graphical interpolation, may be required in order to extrapolate and determine the volume of liquid in the chamber 12.

The device according to the invention is preferably constructed so that it can accommodate an absolute pressure of at least 1000 bar, more preferably of at least 1500 bar in the cell 1. Therefore, the cell 1 can be made of a material such as stainless steel or any other pressure-resistant material such as titanium, nickel-based alloys (Hastelloy), and austenitic nickel-chromium-based superalloys (Inconel).

Figure 4A:
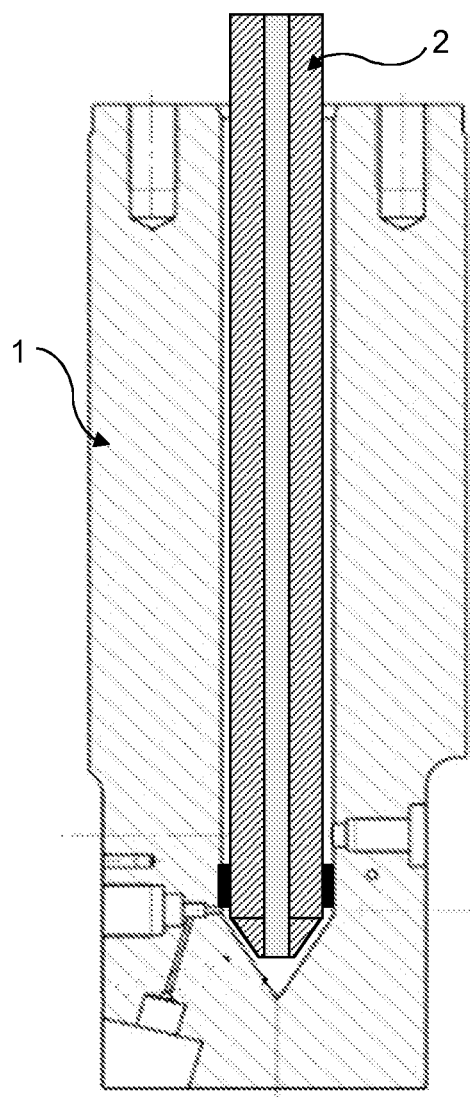
FIGS. 4A and 4B illustrate a cross-sectional view of the cell and piston of the device according to one embodiment of the invention, in two different positions.

As mentioned above, and as illustrated in FIGS. 2, 4A, and 4B the device also comprises a piston 2 which is slidable in the cell 1. Therefore, the piston 2 may be inserted in the cell 1 from the open extremity 6 of the upper part 3 of the cell 1. When the piston 2 is in the cell 1, it seals the cell 1 in a gas-tight manner. Therefore, there is no contact between the internal space 7 (and the chamber 12) of the cell 1 and the external environment. While the piston 2 slides in the cell 1, it can move from a first position wherein the piston 2 is at the most remote position from the cone-shaped closed extremity (FIG. 4B) to a second position wherein the piston 2 is closest to the cone-shaped closed extremity (FIG. 4A). At this second position, part of the piston 2 (its lower part as detailed below) may preferably be inserted in the chamber 12 formed by the conical-shape closed extremity. It goes without saying that the piston 2 can have all intermediate positions between the first and the second position.

The piston 2 can be driven manually, mechanically, electrically or hydraulically. For example, the piston 2 may be driven by using an electrical or hydraulic jack system. In case the piston 2 is driven manually, a worm drive can be used.

The piston 2 comprises an upper part 15 and a lower part 16. The upper part 15 of the piston 2 may have a cylindrical shape with a circular or non-circular base. Preferably, the base is a circular disc.

The upper part 15 of the piston 2 may have a length from 10 to 60 cm, and preferably from 20 to 45 cm. For example, the upper part 15 of the piston 2 may have a length from 10 to 15 cm; or from 15 to 20 cm; or from 20 to 25 cm; or from 25 to 30 cm; or from 30 to 35 cm; or from 35 to 40 cm; or from 40 to 45 cm; or from 45 to 50 cm; or from 50 to 55 cm; or from 55 to 60 cm.

The upper part 15 of the piston 2 may have an outer diameter which is equal to or less than the inner diameter of the upper part 3 of the cell 1, so that the piston 2 can be inserted in the cell 1. Therefore, the outer diameter of the upper part 15 of the piston 2 may be equal to or less than 50 mm. For example, this diameter may be from 5 to 10 mm; or from 10 to 15 mm; or from 15 to 20 mm; or from 20 to 25 mm; or from 25 to 30 mm; or from 30 to 35 mm; or from 35 to 40 mm; or from 40 to 45 mm; or from 45 to 50 mm.

Preferably, the outer diameter of the upper part 15 of the piston 2 is equal to the inner diameter of the upper part 3 of the cell 1.

In some embodiments, the outer shape of the upper part 15 of the piston 2 substantially matches the inner shape of the upper part 3 of the cell 1 (for example they can both have a cylindrical shape with a circular base of the same diameter). However, according to some embodiments, the upper part 15 of the piston 2 may have an outer shape that does not substantially match the inner shape of the upper part 3 of the cell 1 (for example they can both have a cylindrical shape with a circular base, the base of the upper part 15 of the piston 2 having a different outer diameter from the inner diameter of the base of the upper part 3 of the cell 1, or the upper part 3 of the cell 1 can have a cylindrical inner shape with a circular base while the upper part 15 of the piston 2 may have a cylindrical outer shape with a non-circular base). In this case, at least one portion of the length of the upper part 15 of the piston 2 and/or at least one portion of the lower part 16 of the piston 2 may have substantially the same outer diameter as the inner diameter of the upper part 3 of the cell 1, so that the piston 2 can seal in a gas-tight manner the cell 1. In preferred variations, a sealant 20 for example surrounding at least a part of the length of the piston 2, as illustrated in FIG. 2, may be present in order to achieve sealing of the cell 1 in a gas-tight manner. The sealant 20 is preferably present at or proximate to the lower end of the upper part 15 of the piston 2.

According to some preferred embodiments, and as shown in FIG. 2, the upper part 15 of the piston 2 has an outer diameter which is uniform along its length.

According to other embodiments (not illustrated in the figures), the upper part 15 of the piston 2 has an outer diameter which is not uniform along the length of the upper part 15.

The lower part 16 of the piston 2 may have a truncated-cone shape, as illustrated in FIG. 2. By "truncated-cone shape" is meant the shape of a cone truncated by a plane which is preferably parallel to the base of the cone. The truncated-cone shape makes it possible to at least partly slide the piston 2 and more particularly the lower part 16 of the piston 2 within the lower part 4 of the cell 1. The lower part 16 of the piston 2 may have an upper end 17a which is connected to the upper part 15 of the piston 2, and a lower end 17b which is farthest from the upper part 15 of the piston 2 and closest to the cone-shaped closed extremity when the piston 2 is in the cell 1. According to preferred embodiments, the lower end 17b may be a planar surface (as illustrated in FIG. 2). According to other embodiments, the lower end 17b may be provided with at least one recess (not illustrated in the figures).

According to preferred embodiments, the upper part 15 and the lower part 16 of the piston 2 are integrally formed as a single piece.

The lower part 16 of the piston 2 may have a height from 2.5 to 37.5 mm, and preferably from 5 to 35 mm. For example, the lower part 16 of the piston 2 may have a height from 2.5 to 5 mm; or from 5 to 10 mm; or from 10 to 15 mm; or from 15 to 20 mm; or from 20 to 25 mm; or from 25 to 30 mm; or from 30 to 35 mm; or from 35 to 37.5 mm. By "height" is meant the distance from the lower end 17b of the lower part 15 of the piston 2 to the upper end 17a of the lower part 15 of the piston 2.

The lower part 16 of the piston 2 may have an outer diameter that decreases from the upper end 17a to the lower end 17b. The outer diameter at the upper end 17a of the piston 2 may preferably be equal to the diameter of the lower part 4 of the cell 1 at the non-tapered end 10.

At its lower end 17b, the lower part 16 of the piston may have a diameter from 5 to 30 mm.

When the piston is at the second position (and as mentioned above, see FIG. 4A) the lower part 16 of the piston 2 (at least partially) is preferably located in the chamber 12 of the cell 1.

According to some embodiments, the ratio of the height of the lower part 16 of the piston 2 to the height of the lower part 4 of the cell 1 (along the longitudinal axis) is from 0.1 to 0.8, and preferably from 0.3 to 0.7. For example, this ratio may be from 0.1 to 0.2; or from 0.2 to 0.3; or from 0.3 to 0.4; or from 0.4 to 0.5; or from 0.5 to 0.6; or from 0.6 to 0.7; or from 0.7 to 0.8.

As explained above, when the upper part 15 of the piston 2 has an outer shape that does not match the inner shape of the upper part 3 of the cell 1, and more particularly when the upper part 15 of the piston 2 has a smaller outer diameter than the inner diameter of the upper part 3 of the cell 1, at least one portion of the lower part 16 of the piston 2 may have an outer diameter equal to the inner diameter of the upper part 3 of the cell 1, so that the piston 2 can seal in an gas-tight manner the cell 1.

For example, the lower part 16 of the piston 2 may have an outer diameter at its upper end 17a which is equal to the inner diameter of the upper part 15 of the cell 1.

Furthermore, the lower part 16 of the piston 2, and more particularly the lower end 17b of the piston 2 may comprise a window 18. This window 18 may be oriented towards the cone-shaped closed extremity and therefore towards the chamber 12. The presence of the window 18 makes it possible to monitor from the outside the content of the cell 1 owing to a monitoring system (which is described below). Therefore, the window 18 (along with the monitoring system) allows the visualization of the chamber 12 comprising the liquid, in order to determine the level of the liquid in the chamber 12. This may be carried out for example by reading the markings 14 on the peripheral surface 13 of the cone-shaped closed extremity.

The window 18 may be for example made of sapphire or any other transparent or translucid material able to withstand high pressure, high temperature and corrosion.

According to some embodiments, and as shown in FIG. 2, the lower end 17b of the piston 2 is a planar surface, and the window 18 covers part of this planar surface.

According to other embodiments, the window 18 may be located in a recess formed on the lower end 17b.

According to other embodiments, the window 18 covers the entire surface of the lower end 17b of the piston 2.

The device may further comprise an endoscope 19 arranged within the piston 2. The endoscope may be configured to connect the window 18 with a monitoring system detailed below in order to establish an optical connection between the window 18 and the monitoring system. By "endoscope" is meant a tubular system comprising a number of lenses which make it possible to "transfer" the image from the window 18 to the monitoring system. The device may also comprise a system for illuminating the cell 1 arranged in the piston 2, such as an optic fiber (not illustrated in the figures) which may transmit light between the monitoring system and the window 18 so as to facilitate the visualization of content of the cell 1. The illumination may be performed with white light or non-white light. The light spectrum used for the illumination may be adjusted in order to facilitate the visualization of the liquid meniscus. When a camera is used to record images of the cell 1, image processing, such as contrast adjustment, may be performed.

Furthermore, the device according to the invention, and more particularly the cell 1 described above, may comprise at least one pressure sensor which can detect the pressure in the cell 1.

Optionally, the device may comprise a purge system for purging the interior of the cell 1 from any material present therein.

According to some embodiments the device according to the invention may be part of an assembly. This assembly may comprise for example, the device as well as a monitoring system (not illustrated in the figures) such as a camera for example, in order to visualize the content of the cell 1. According to preferred embodiments, the monitoring system is located outside the cell 1.

Advantageously, the fact that the window 18, the monitoring system and/or the endoscope 19 are not located in the chamber 12 of the cell 1 makes it possible to minimize any dead volumes and therefore increase the accuracy of the measurement.

The assembly may further comprise an enclosure (not illustrated in the figures) which may surround the cell 1. The enclosure may be made from a material chosen from steel, aluminum, or a composite material. It is preferable that the enclosure is insulated to avoid for example temperature loss. The enclosure makes it possible to provide a regulated and uniform temperature in the cell 1. Therefore, the interior of the chamber 12 has the same temperature as the internal space 7 defined by the tubular sidewall 5 of the upper part 3 of the cell 1. This allows to avoid for example possible unwanted condensations of the hydrocarbon fluid.

According to preferred embodiments, the monitoring system detailed above is located outside the enclosure in order to protect it from high temperatures.

The assembly according to the invention may comprise at least one temperature sensor (such as thermocouples) and/or a temperature regulation system, which may comprise a heating and/or a cooling system. For example, use can be made of a refrigerant circuit and/or resistive heating. According to some embodiments, the temperature sensor(s) and/or the temperature regulation system may be located in the cell 1. According to other embodiments, the temperature sensor(s) and/or the temperature regulation system may be located outside cell 1 and inside the enclosure. Still according to other embodiments, both the cell 1 and the enclosure may be provided with a temperature sensor and/or a temperature regulation system.

According to some embodiments, the assembly, and more particularly the enclosure may comprise one or more additional cells (different from cell 1). These cells may be used for example for measurements carried out on a hydrocarbon oil or a gas coming from the hydrocarbon fluid. These additional cells may be connected to the cell 1 so that at least an amount of the hydrocarbon fluid sample may be transferred from the cell 1 to the additional cell(s), or vice versa.

The device of the invention or the assembly may also comprise—or be associated in a larger system with—an analysis module and/or a control module. The analysis module may receive data from the pressure and/or temperature sensors, from the monitoring system, from the user and/or from the control module and provide analysis data as an output.

The control module may receive data from the user and/or from the analysis module and may send instructions which make it possible to actuate the piston as well as the various valves of the device. It is possible to operate the device in an automated or semi-automated manner, using appropriate computer hardware and software.

Method for Determining the Volume of Liquid

The invention further provides a method for determining a volume of liquid in a hydrocarbon fluid sample. This method is implemented in the device described above.

The hydrocarbon fluid is preferably a hydrocarbon fluid recovered from a subterranean formation. It is preferably a complex fluid comprising various hydrocarbon compounds and optionally water as well as contaminants or chemicals used in the process of hydrocarbon recovery (surfactants, carbon dioxide, nitrogen, etc.).

According to preferred embodiments, the hydrocarbon fluid is a gas condensate. By "gas condensate" is meant a low-density mixture of hydrocarbon liquids that are present as gaseous components in the raw natural gas recovered from the subterranean formation. For example, a gas condensate may comprise carbon dioxide and/or nitrogen as well as hydrocarbon compounds having from 1 to 500 carbon atoms.

However, it will be understood that the device according to the invention may also be used for other types of fluids, in particular complex fluids comprising a mixture of different chemical compounds.

The method comprises a first step of introducing the hydrocarbon fluid sample in the cell 1 described above. However, prior to introducing the hydrocarbon fluid sample in the cell 1, the cell 1 may be heated (for example by using the temperature regulation system mentioned above), in order for example to obtain in the internal space 7 (and the chamber 12) of the cell 1 a temperature proximate to the temperature of the subterranean reservoir. Therefore, the cell 1 may be kept, and in particular may be heated at a temperature from 15 to 200° C., and preferably from 80 to 180° C. For example, this temperature may be from 15 to 20° C.; or from 20 to 30° C.; or from 30 to 40° C.; or from 40 to 50° C.; or from 50 to 60° C.; or from 60 to 70° C.; or from 70 to 80° C.; or from 80 to 90° C.; or from 90 to 100° C.; or from 100 to 110° C.; or from 110 to 120° C.; or from 120 to 130° C.; or from 130 to 140° C.; or from 140 to 150° C.; or from 150 to 160° C.; or from 160 to 170° C.; or from 170 to 180° C.; or from 180 to 190° C.; or from 190 to 200° C.

Furthermore, upon introduction of the hydrocarbon fluid sample in the cell 1, the cell 1 may be pressurized. For example, the cell 1 may be pressurized to an initial pressure from 10 to 2 000 bar, and preferably from 10 to 1 500 bar. The cell may notably be pressurized to an initial pressure from 10 to 100 bar; or from 100 to 200 bar; or from 200 to 300 bar; or from 300 to 400 bar; or from 400 to 500 bar; or from 500 to 600 bar; or from 600 to 700 bar; or from 700 to 800 bar; or from 800 to 900 bar; or from 900 to 1 000 bar; or from 1 000 to 1 100 bar; or from 1 100 to 1 200 bar; or from 1 200 to 1 300 bar; or from 1 300 to 1 400 bar; or from 1 400 to 1 500 bar; or from 1 500 to 1 600 bar; or from 1 600 to 1 700 bar; or from 1 700 to 1 800 bar; or from 1 800 to 1 900 bar; or from 1 900 to 2 000 bar.

According to preferred embodiments, this initial pressure is higher than the pressure observed in the subterranean formation. Preferably the initial pressure in the cell 1 is higher than the pressure observed in the subterranean formation by at least 100 bar, and preferably at least 150 bar.

The pressure of the hydrocarbon fluid in the cell 1 at the introduction stage can be achieved directly owing to the pressure of the source of hydrocarbon fluid, notably if the device is placed within an extraction well so as to collect hydrocarbon fluid from the subterranean formation in situ, or if the cell 1 is connected via its fluid inlet 8 and via a conduit or a tube to a vessel under pressure comprising the hydrocarbon fluid.

At this step, the hydrocarbon fluid in the cell 1 is preferably a gaseous fraction; it preferably does not comprise any liquid fraction.

After the introduction step, the method comprises a step of decreasing the pressure inside the cell 1, in order to form an amount of liquid in the chamber 12. During this step, it is preferable that the temperature in the cell 1 remains constant. For example, this temperature can be from 15 to 200° C., and preferably from 20 to 180° C.

Figure 4B:
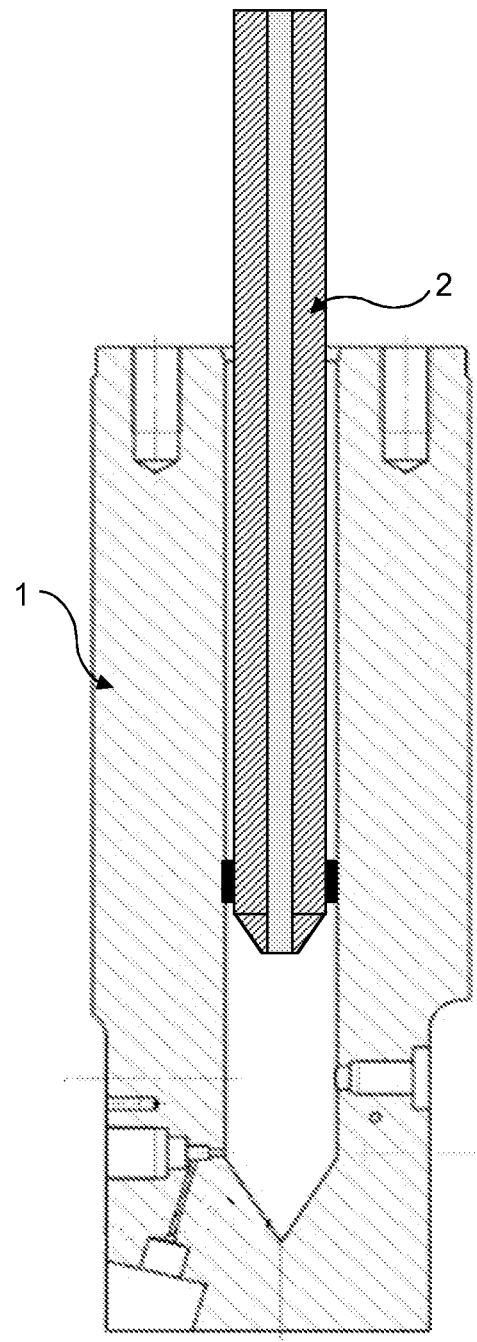

The decrease of the pressure can be achieved by sliding the piston 2 to a direction from the second position (as illustrated on FIG. 4A) to the first position (as illustrated on FIG. 4B). The pressure may be decreased by one on or more decrements. Each decrement may be for example from 0.1 to 50 bar, preferably from 0.5 to 20 bar, and preferably from 1 to 10 bar, relative to the initial pressure inside the cell 1. For example, each decrement may be from 0.1 to 0.5 bar; or from 0.5 to 1 bar; or from 1 to 5 bar; or from 5 to 10 bar; or from 10 to 15 bar; or from 15 to 20 bar; or from 20 to 25 bar; or from 25 to 30 bar; or from 30 to 35 bar; or from 35 to 40 bar; or from 40 to 45 bar; or from 45 to 50 bar, relative to the initial pressure inside the cell 1.

Due to this decompression, an amount of liquid (liquid fraction) is formed from the hydrocarbon fluid sample (gaseous fraction). More particularly, the expansion of the hydrocarbon fluid continues until the hydrocarbon compounds in the gaseous fraction start to condensate. The point at which the hydrocarbon components start to condense out of the gaseous fraction is called "dew point".

In the preferred case where the hydrocarbon fluid is a gas condensate, the liquid comprises at first only part of hydrocarbons having from 1 to 100 carbon atoms, while the rest of the hydrocarbons having from 1 to 100 carbon atoms remain in the gaseous fraction along with the gas ($N_2$ and/or $CO_2$). The more the pressure decreases, the more the amount of liquid in the chamber 12 increases.

The method then comprises a step of measuring the volume of liquid present in the cell 1. This measurement may be carried out by visually monitoring the chamber 12 and more particularly by observing the level of liquid in the chamber 12 (in the cone-shaped closed extremity), in other words by determining the position of the interface between the liquid and the gaseous fraction on the peripheral surface 13 of the cone-shaped closed extremity which is connected to the monitoring system via the endoscope 19.

This visual monitoring may be carried out through the window 18 of the piston 2.

More particularly, the markings 14 on the peripheral surface 13 of the cone-shaped closed extremity facilitate the reading (visualization) of the diameter of the cone corresponding to the height of liquid in the chamber 12 (interface between the liquid and the gaseous fraction). Then, by using this diameter, the volume of the liquid contained in the chamber 12 may be calculated.

The presence of the markings 14 makes it possible to increase the accuracy of the method. In fact, at high temperature, the endoscope 18 comprised in the piston 2 may be deformed, therefore also deforming the image of the chamber 12 received by the monitoring system. The markings 14 thus facilitate the calibration of the device in order to increase the precision of the measurement.

The step of decreasing the pressure in the cell 1 as well as the step of measuring the volume of liquid formed in the chamber 12 may be repeated a plurality of times, for instance from 5 to 500 times, preferably from 10 to 400 times, and more preferably from 20 to 200 times. During each repetition, the pressure in the cell 1 is decreased as explained above in order to form another quantity of liquid in the chamber 12.

According to some preferred embodiments, during these repetitions, the temperature in the cell is constant.

According to other embodiments, during these repetitions, the temperature in the cell may vary, for example the temperature may increase or decrease.

According to other embodiments, the method is not implemented in situ. In this case, the method is implemented by using a hydrocarbon fluid which has been recovered from a subterranean formation.

The method makes it possible to measure volumes of liquid equal to or lower than 1 000 µL, preferably equal to or lower than 500 µL, preferably equal to or lower than 50 µL, preferably equal to or lower than 50 µL, preferably equal to or lower than 10 µL, preferably equal to or lower than 1 µL, preferably equal to or lower than 0.5 µL, and preferably equal to or lower than 0.2 µL. For example, the measured volume may be from 0.1 to 0.2 µL; or from 0.2 to 0.5 µL; or from 0.5 to 1 µL; or from 1 to 5 µL; or from 5 to 10 µL; or from 10 to 25 µL; or from 25 to 50 µL; or from 50 to 75 µL; or from 75 to 100 µL; or from 100 to 150 µL; or from 150 to 200 µL; or from 200 to 250 µL; or from 250 to 300 µL; or from 300 to 350 µL; or from 350 to 400 µL; or from 400 to 450 µL; or from 450 to 500 µL; or from 500 to 550 µL; from 550 to 600 µL; or from 600 to 650 µL; or from 650 to 700 µL; or from 700 to 750 µL; from 750 to 800 µL; or from 800 to 850 µL; or from 850 to 900 µL; or from 900 to 950 µL; or from 950 to 1 000 µL.

The method also makes it possible to measure the dew point of the hydrocarbon fluid introduced in the cell 1.

Furthermore, this method makes it possible to measure the vapor pressure of the hydrocarbon fluid with accuracy. By "vapor pressure" is meant the pressure exerted by a vapor in thermodynamic equilibrium with its condensed phases (solid or liquid) at a given temperature in a closed system.

The invention claimed is:

1. A device for determining a volume of liquid in a hydrocarbon fluid sample, the device including:
    a cell comprising an upper part defined by a tubular sidewall and a lower part defined by a cone-shaped closed extremity, the lower part forming a chamber configured to receive the liquid; and
    a piston comprising an upper part, a lower part, and a window oriented towards the cone-shaped closed extremity of the cell, the piston being slideable in the cell and sealing the cell in a gas-tight manner.

2. The device according to claim 1, wherein the closed extremity of the cell has an aperture from 30° to 120°.

3. The device according to claim 1, wherein the lower part of the cell comprises at least one marking on a peripheral surface of the cone-shaped closed extremity.

4. The device according to claim 3, wherein each marking is in a form of a circular arc.

5. The device according to claim 3, wherein the at least one markings is arranged in one or several conical sectors on the peripheral surface of the cone-shaped closed extremity.

6. The device according to claim 5, wherein the at least one marking is arranged in two conical sectors on the peripheral surface of the cone-shaped closed extremity.

7. The device according to claim 1, wherein the lower part of the piston has a truncated-cone shape in order to be partly slideable within the lower part of the cell.

8. The device according to claim 1, wherein the piston comprises an endoscope configured to connect the window with a monitoring system.

9. The device according to claim 1, wherein a system for illuminating the cell is arranged in the piston.

10. The device according to claim 1, wherein the upper part of the cell comprises at least one fluid inlet and at least one fluid outlet.

11. An assembly comprising:
    (a) a device for determining a volume of liquid in a hydrocarbon fluid sample, the device including:
        a cell comprising an upper part defined by a tubular sidewall and a lower part defined by a cone-shaped closed extremity, the lower part forming a chamber configured to receive the liquid; and
        a piston comprising an upper part, a lower part, and a window oriented towards the cone-shaped closed extremity of the cell, the piston being slideable in the cell and sealing the cell in a gas-tight manner; and
    (b) a monitoring system for visually monitoring contents of the chamber.

12. The assembly according to claim 11, comprising a temperature-regulated enclosure surrounding the cell.

13. The assembly according to claim 11, comprising at least one temperature sensor.

14. A method for determining volume of a liquid in a hydrocarbon fluid sample, the method comprising:
   introducing a hydrocarbon fluid sample into a cell of a device for determining a volume of liquid in the hydrocarbon fluid sample, the device including:
      the cell comprising an upper part defined by a tubular sidewall and a lower part defined by a cone-shaped closed extremity, the lower part forming a chamber configured to receive the liquid; and
      a piston comprising an upper part, a lower part, and a window oriented towards the cone-shaped closed extremity of the cell, the piston being slideable in the cell and sealing the cell in a gas-tight manner;
   decreasing pressure inside the cell by sliding the piston in the cell; and
   measuring the volume of liquid present in the chamber.

15. The method according to claim 14, wherein the hydrocarbon fluid is a gas condensate.

16. The method according to claim 14, wherein the pressure is decreased by one or more decrements, each decrement being from 0.1 to 50 bar relative to initial pressure inside the cell.

17. The method according to claim 14, wherein the measuring the volume of liquid is carried out by visually monitoring the chamber and determining position of a liquid-gas interface on a peripheral surface of the cone-shaped closed extremity.

18. The method according to claim 17, wherein visually monitoring the chamber is carried out through the window of the piston, or wherein the position of the liquid-gas interface is determined owing to at least one marking present on the peripheral surface of the cone-shaped closed extremity.

19. The method according to claim 14, wherein the decreasing the pressure and the measuring the volume of liquid are repeated a plurality of times.

\* \* \* \* \*

UNITED STATES PATENT AND TRADEMARK OFFICE
CERTIFICATE OF CORRECTION

PATENT NO. : 12,078,521 B2
APPLICATION NO. : 17/612823
DATED : September 3, 2024
INVENTOR(S) : Gilles Couchou-Meillot It is certified that error appears in the above-identified patent and that said Letters Patent is hereby corrected as shown below:

In the Claims

In Claim 5 at Column 14, Line 39, after the first occurrence of "one", delete "markings" and insert -- marking --.

Signed and Sealed this
Twenty-second Day of October, 2024

Katherine Kelly Vidal
*Director of the United States Patent and Trademark Office*